US011964161B2

United States Patent
Kim et al.

(10) Patent No.: US 11,964,161 B2
(45) Date of Patent: Apr. 23, 2024

(54) PLASMA GENERATOR

(71) Applicant: GCS Co., Ltd., Seongnam-si (KR)

(72) Inventors: Chang Sik Kim, Gyeonggi-do (KR); Tae Yong Kim, Seoul (KR); Myeong Woo Kim, Gyeonggi-do (KR); Hyuk Namgoong, Gyeonggi-do (KR); Ha Yun Lee, Gyeonggi-do (KR)

(73) Assignee: GCS Co., Ltd., Seongnam-si (KR)

( * ) Notice: Subject to any disclaimer, the term of this patent is extended or adjusted under 35 U.S.C. 154(b) by 0 days.

(21) Appl. No.: 18/230,169

(22) Filed: Aug. 4, 2023

(65) Prior Publication Data
US 2024/0042224 A1    Feb. 8, 2024

(30) Foreign Application Priority Data

Aug. 5, 2022  (KR) .................. 10-2022-0097828

(51) Int. Cl.
*A61N 1/44* (2006.01)
*B01D 53/04* (2006.01)
*H05H 1/26* (2006.01)

(52) U.S. Cl.
CPC ............ *A61N 1/44* (2013.01); *B01D 53/0446* (2013.01); *H05H 1/26* (2013.01); *B01D 2253/102* (2013.01); *B01D 2257/106* (2013.01); *H05H 2245/10* (2021.05); *H05H 2245/34* (2021.05); *H05H 2245/60* (2021.05)

(58) Field of Classification Search
None
See application file for complete search history.

(56) References Cited

U.S. PATENT DOCUMENTS

| 11,045,246 | B1* | 6/2021 | Schwartz | A61F 5/4553 |
| 11,246,951 | B2* | 2/2022 | Neister | A61L 2/0011 |
| 2005/0143793 | A1* | 6/2005 | Korman | A61N 5/0616 607/94 |
| 2006/0104858 | A1* | 5/2006 | Potember | A61L 9/205 422/123 |
| 2009/0143842 | A1* | 6/2009 | Cumbie | A61N 5/0624 600/365 |

(Continued)

FOREIGN PATENT DOCUMENTS

| KR | 10-2019-0015662 A | 2/2019 |
| KR | 10-2019-0018025 A | 2/2019 |

(Continued)

OTHER PUBLICATIONS

Machine translation KR-20190041874-A, 2024 Clarivate Analytics (Year: 2024).*

(Continued)

*Primary Examiner* — Carl H Layno
*Assistant Examiner* — Manolis Pahakis
(74) *Attorney, Agent, or Firm* — Nicholas Park

(57) ABSTRACT

Disclosed is a plasma generator. The plasma generator may include a gripping portion including at least one interface unit configured to receive an input from a user; a head portion including a plasma generating portion configured to generate the plasma; a first cartridge configured to detachably couple at a first end of the head portion and generate the plasma over a predetermined region; and a light irradiation portion provided at a second end of the head portion.

10 Claims, 13 Drawing Sheets

(56) References Cited

U.S. PATENT DOCUMENTS

| | | | | |
|---|---|---|---|---|
| 2010/0296969 A1* | 11/2010 | Ngo | ............... | A61L 2/0094 |
| | | | | 422/33 |
| 2012/0275960 A1* | 11/2012 | Seck | ............... | A62B 15/00 |
| | | | | 422/121 |
| 2015/0007856 A1* | 1/2015 | Jackson | ............... | G03F 7/422 |
| | | | | 134/1 |
| 2015/0037201 A1* | 2/2015 | Armour | ............... | A61B 90/06 |
| | | | | 600/203 |
| 2017/0080246 A1* | 3/2017 | Knight | ............... | A61G 10/02 |
| 2020/0315682 A1* | 10/2020 | Ahn | ............... | A61B 18/042 |
| 2023/0040683 A1* | 2/2023 | Zhang | ............... | H05H 1/48 |

FOREIGN PATENT DOCUMENTS

| | | | | |
|---|---|---|---|---|
| KR | 10-2019-0041874 A | | 4/2019 | |
| KR | 20190041874 A | * | 4/2019 | ............... A61N 1/44 |
| KR | 102037811 B1 | * | 10/2019 | ............... A61N 1/44 |
| KR | 10-2020-0058003 A | | 5/2020 | |
| KR | 20210049405 A | * | 5/2021 | ........... H05H 1/2406 |
| KR | 20220099213 A | * | 7/2022 | ............ A61M 35/30 |
| WO | WO-2017179819 A1 | * | 10/2017 | ............. A45D 44/00 |

OTHER PUBLICATIONS

Machine translation for KR 102037811-B1, 2024 Clarivate Analytics (Year: 2024).*

Machine translation for KR 20210049405-A, 2024 Clarivate Analytics (Year: 2024).*

Machine translation for KR 20220099213-A, 2024 Clarivate Analytics (Year: 2024).*

Machine translation for WO 2017179819 A1, 2024 Clarivate Analytics (Year: 2024).*

* cited by examiner

PLASMA GENERATOR

CROSS-REFERENCE TO RELATED APPLICATION

This application claims priority from and the benefit of Korean Patent Application No. 10-2022-0097828 filed on Aug. 5, 2022, which is hereby incorporated by reference in its entirety.

BACKGROUND

Technical Field

The present disclosure relates to a plasma generator and more particularly, to a device for irradiating plasma to the skin of an animal using a plasma generator.

Related Art

From the survey conducted in the year of 2021, it is estimated that 29.7% of all households in Korea are raising pets. A relationship between pets and humans is mutually beneficial and dynamic and, particularly, is known to improve human health and quality of life. Results show that a group raising pets has lower levels of stress and reduced risk of heart disease and feelings of depression, and a stronger immune system.

However, raising a pet may require more time and effort than people think. The pet needs to be fed on time. Also, there is a need to purchase snacks, nets, or toys, and to go for a walk periodically. In addition to time, a lot of financial expenses not expected before adopting the pet may occur. In particular, unlike people, pets lack insurance so a single hospital visit may cost a lot of money.

Pets may visit the hospital for treatment of skin disease, prevention of parasitic infection, or disease caused by old age. Among them, the skin disease may be the main factor for the pets to visit the hospital. The hair present in a pet, such as a cat and a dog, may prevent air from circulating through the skin of the pet. Accordingly, when moisture penetrates into the hair, various skin diseases or odor may be developed.

Also, the skin may also be present on the inside of the ear. In particular, the structure of ears of pets may be somewhat more complex than that of humans and long hair may be present in the ears. Accordingly, the ears of a pet are more prone to the skin disease and it may be difficult for a corresponding owner to manage the same. Therefore, there may be a demand for a device through which an owner of a pet may directly manage the skin of the pet.

Reference material includes Korean Patent Laid-Open Publication No. 10-2019-0018025.

SUMMARY

The present disclosure is conceived to outperform the aforementioned related art and provides a plasma generator for irradiating plasma to the skin of an animal.

Technical objects set forth herein are not limited to the aforementioned technical objects and other technical objects not described herein may be clearly understood by one of ordinary skill in the art from the following description.

According to an example embodiment of the present disclosure to solve the aforementioned objects, there is provided a plasma generator. The plasma generator may include a gripping portion including at least one interface unit configured to receive an input from a user; a head portion including a plasma generating portion configured to generate the plasma; a first cartridge configured to detachably couple at a first end of the head portion and generate the plasma over a predetermined region; and a light irradiation portion provided at a second end of the head portion.

Also, the at least one interface unit may include a first interface unit configured to receive the input from the user for controlling the first cartridge; and a second interface unit configured to receive the input from the user for controlling the light irradiation portion.

Also, the first cartridge may include a first operating portion configured to irradiate the plasma to a region that faces a first operation surface through the first operation surface; and a first coupling portion configured to couple to the first operating portion and detachably couple to the head portion. The first coupling portion may include a first edge frame formed to be detachable to edge of the first end of the head portion; and a plurality of first protruding portions formed in the first edge frame and configured to couple to a side surface of the first operating portion, the plurality of first protruding portions being formed in the first edge frame to not protrude forward of the first operating portion.

Also, the plasma generator may further include a second cartridge configured to detachably couple at the first end of the head portion and generate the plasma over the predetermined region. The second cartridge may include a second operating portion configured to irradiate the plasma to a region that faces a second operation surface through the second operation surface; and a second coupling portion configured to couple to the second operating portion and detachably couple to the head portion, and the second coupling portion may include a second edge frame formed to be detachable to edge of the first end of the head portion; and a plurality of second protruding portions formed in the second edge frame and configured to couple to a side surface of the second operating portion, the plurality of second protruding portions formed in the second edge frame to protrude forward of the second operating portion.

Also, the plasma generator may further include a third cartridge configured to detachably couple at the first end of the head portion and to generate the plasma over the predetermined region. The third cartridge may include a third operating portion configured to irradiate the plasma to a region that faces a predetermined third operation surface through the third operation surface; and a third coupling portion configured to couple to the third operating portion and to detachably couple to the head portion, and the third operation surface may include a (3-1)-th operation surface; and a (3-2)-th operation surface corresponding to a surface of a protruding pillar that protrudes from the (3-1)-th operation surface.

Also, the light irradiation portion may include at least one first light emitting diode (LED) using a first wavelength of 355 nm to 455 nm; at least one first laser diode (LD) using a second wavelength of 640 nm to 655 nm; and at least one second LED using a third wavelength of 660 nm to 670 nm.

Also, the head portion may include an ozone removal portion for removing ozone ($O_3$) that is generated as the plasma is irradiated to the skin.

Also, the ozone removal portion may include a suction fan for sucking the ozone; and an ozone filtering portion for removing the sucked ozone.

Also, the ozone filtering portion may include an ozone filter configured to remove the ozone; and a first filter case configured to fix the ozone filter.

Also, the ozone filtering portion may include a plurality of carbon beads configured to remove the ozone; and a second filter case configured to fix the carbon beads.

Also, the plasma generating portion may include a connecting portion configured to protrude from one surface that faces the first operating portion for connection to the first operating portion, and the ozone filtering portion may be provided to between the plasma generating portion and the first operating portion and may include a hollow through which the connecting portion passes.

Also, the plurality of first protruding portions may be configured to couple to a side surface of the first operating portion at preset intervals such that the ozone is sucked according to an operation of the suction fan.

Technical solutions achievable from the present disclosure are not limited to the aforementioned solutions and other solutions not described herein may be clearly understood by one of ordinary skill in the art to which the present disclosure pertains from the following description.

According to some example embodiments, it is possible to provide a plasma generator capable of managing the skin of an animal.

Effects achievable from the present disclosure are not limited to the aforementioned effects and other effects not described herein may be clearly understood by one of ordinary skill in the art to which the present disclosure pertains from the following description.

BRIEF DESCRIPTION OF THE FIGURES

Various aspects are described with reference to the accompanying drawings and, herein, like reference numerals refer to like elements throughout. In the following example embodiments, numerous specific details are set forth herein to provide thorough understanding of at least one aspect for the purpose of explanation. However, it will be apparent that such aspect(s) may be practiced without the specific details. In other examples, known structures and devices are illustrated in a form of a block diagram to easily describe at least one aspect.

DETAILED DESCRIPTION

Figure 1:
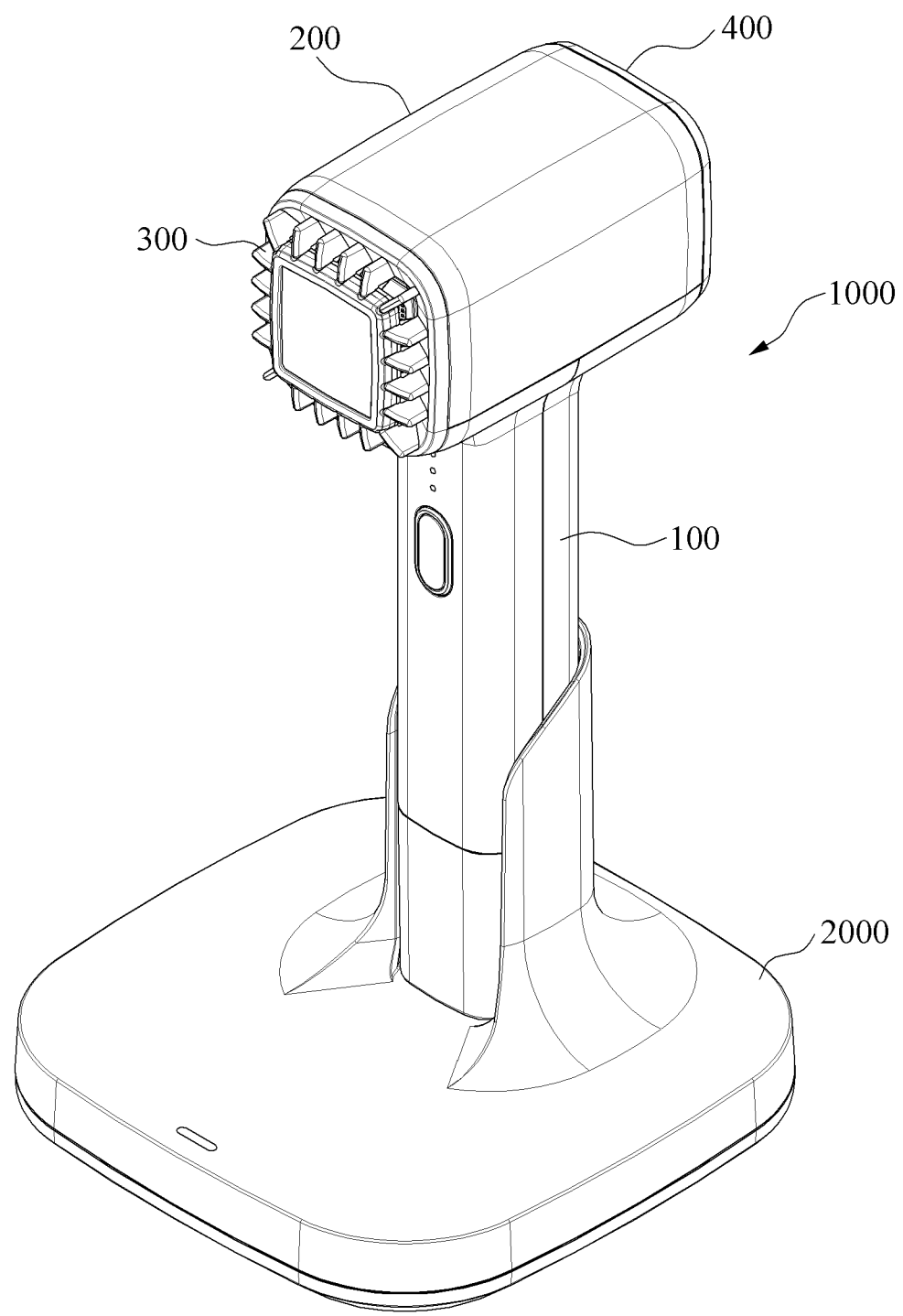
FIG. 1 is a perspective view illustrating an example of a plasma generator according to some example embodiments of the present disclosure.

Various modifications and changes may be made to the present disclosure and the disclosure may include various example embodiments. Specific example embodiments are described in detail with reference to the accompanying drawings. The example embodiments, however, may be embodied in various different forms, and should not be construed as being limited to only the specific example embodiments. Rather, the example embodiments should be understood to include all of the modifications, equivalents, and substitutions included in the spirit and technical scope of the disclosure. Like reference numerals refer to like elements throughout to describe each drawing.

Although the terms "first," "second," "A," "B," etc., may be used herein to describe various components, the components should not be limited by these terms. These terms are only used to distinguish one component from another component. For example, a first component may also be termed a second component and, likewise, a second component may be termed a first component, without departing from the scope of this disclosure. As used herein, the term "and/or" includes any and all combinations of one or more of the associated items.

When a component is referred to as being "connected to" or "accessed to" another component, the component may be directly connected to or accessed to the other component, or one or more other intervening components may be present. In contrast, when a component is referred to as being "directly connected to" or "directly accessed to," there is no intervening component.

The terms used herein are used to simply explain specific example embodiments and are not construed to limit the present disclosure. The singular forms "a," "an," and "the," are intended to include the plural forms as well, unless the context clearly indicates otherwise. It will be further understood that the terms "comprises/comprising (incudes/including)," and "has/having" when used in this specification, specify the presence of stated features, integers, steps, operations, elements, and/or components, but do not preclude the presence or addition of one or more other features, integers, steps, operations, elements, components, and/or groups, thereof.

Unless otherwise defined, all terms including technical and scientific terms used herein have the same meaning as commonly understood by one of ordinary skill in the art to which the present disclosure pertains. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Herein, a plasma generator may be a device for a user to irradiate plasma to the skin of a pet. The plasma may be an ionized gas and a fourth state of a material that follows solid, liquid, and gas. In general, plasma may be generated based on discharge of high voltage and may be used for the purpose of treatment and shaping of an epidermal portion of the skin due to a sublimation action when induced to the skin of a pet. Here, the sublimation action may refer to a phase transition phenomenon in which a substance changes from a solid to a gas without going through a liquid process in chemistry. A user may promote a skin cell regeneration cycle or perform sterilization by irradiating plasma to the skin of the pet through the plasma generator.

Meanwhile, according to some example embodiments of the present disclosure, the plasma generator may include a cartridge replaceably coupled to irradiate plasma to the skin of a pet using various methods. For example, the plasma generator may include a first cartridge for irradiating plasma to the skin of a short-haired pet. The plasma generator may include a second cartridge for irradiating plasma to the skin of a long-haired pet. The plasma generator may include a third cartridge for irradiating plasma to the skin with curves, such as a toe. The user may manage the skin of the pet by selecting an appropriate cartridge from among the first to the third cartridges.

Also, the plasma generator may include a light irradiation portion for reducing bacteria or fungi present in ears of the pet. The user may prevent generation of bacteria or fungi or may reduce the already generated bacteria or fungi by irradiating light to the inside of the ear of the pet through the light irradiation portion. Hereinafter, the plasma generator according to the present disclosure will be described with reference to FIGS. 1 to 7.

Figure 2A:
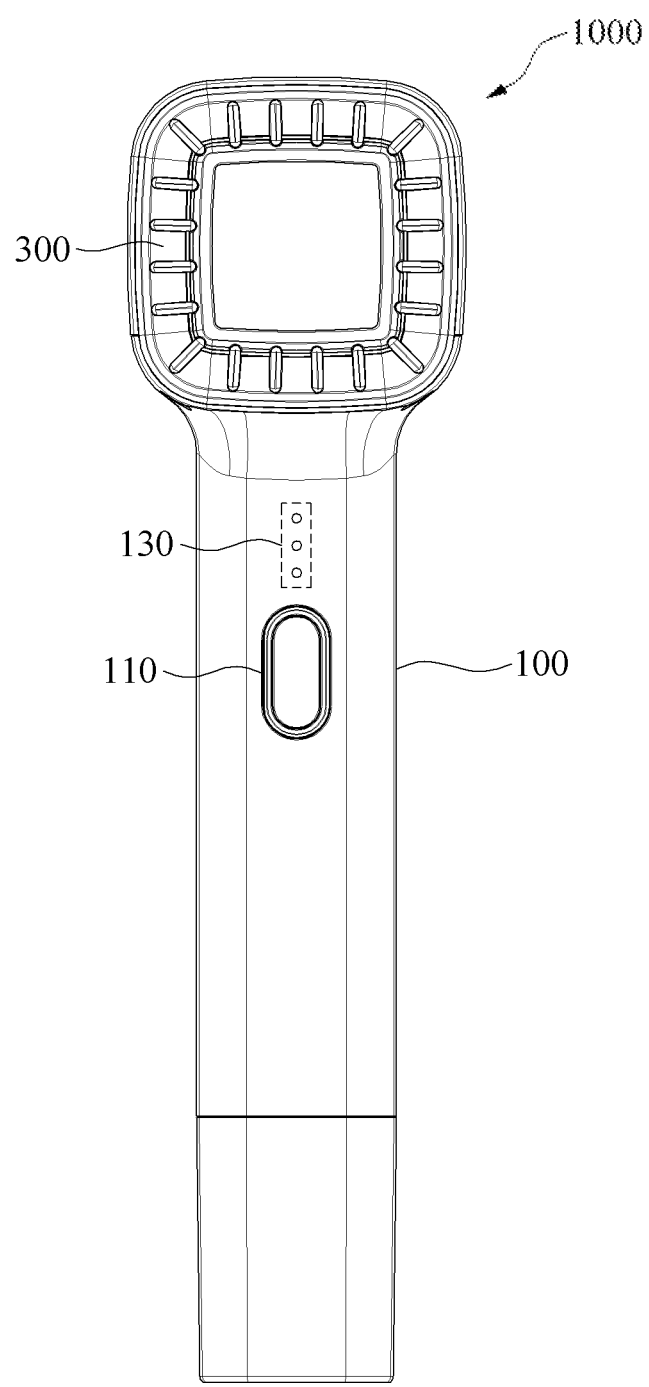
FIGS. 2A and 2B illustrates an example of a plasma generator according to some example embodiments of the present disclosure.
Figure 2B:
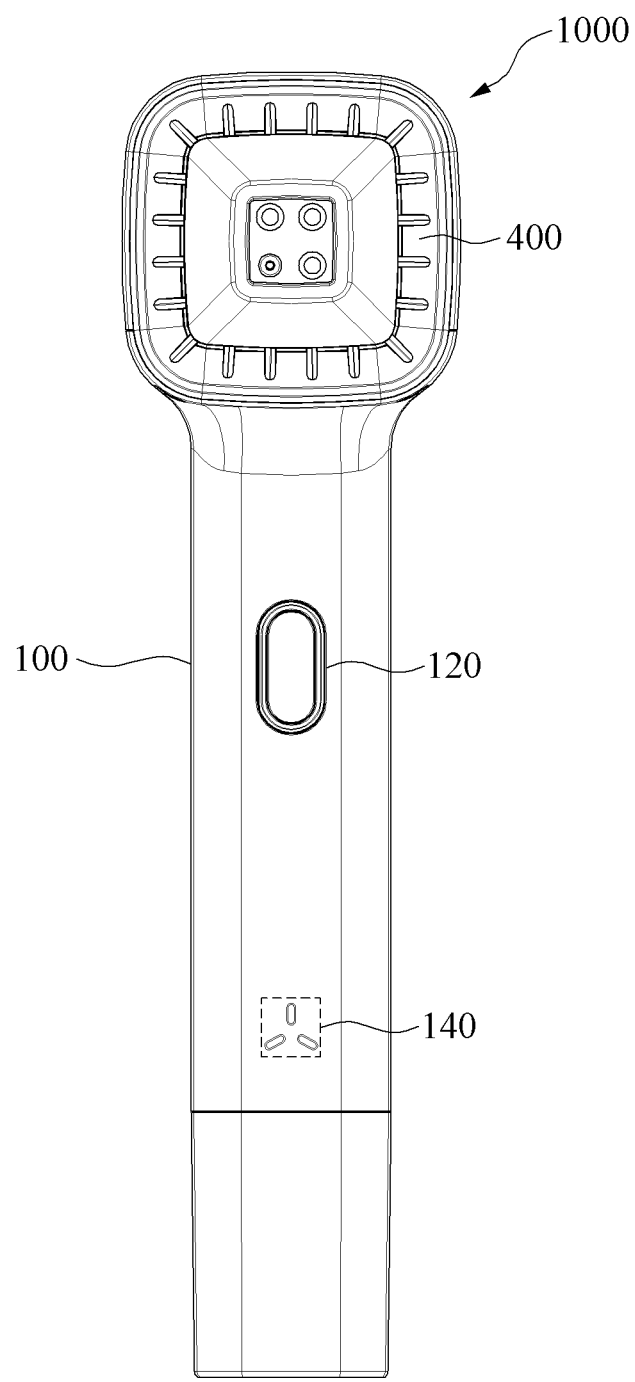

FIG. 1 is a perspective view illustrating an example of a plasma generator according to some example embodiments of the present disclosure. FIGS. 2A and 2B illustrates an example of a plasma generator according to some example embodiments of the present disclosure.

Referring to FIGS. 1, 2A and 2B, a plasma generator 1000 may include a gripping portion 100, a head portion 200, a first cartridge 300, and a light irradiation portion 400. The aforementioned components are not essential to implement the plasma generator 1000 and the plasma generator 1000 may include more or less components than the components listed above.

The gripping portion 100 may be formed in a shape capable of being gripped by a user. The gripping portion 100 may be formed in a shape that allows the user to easily grip the plasma generator 1000.

The gripping portion 100 may include at least one interface unit, a light output portion 130, and a sound output portion 140.

The at least one interface unit may receive an input from the user. The at least one interface unit may be implemented as at least one of a key pad, a dome switch, a touch pad (static pressure/capacitive), a jog wheel, and a jog switch. The at least one interface unit may include a first interface unit 110 and a second interface unit 120.

The first interface unit 110 may be provided below at least one cartridge and may receive the input from the user for controlling the at least one cartridge.

In detail, the plasma generator 1000 according to the present disclosure may include the first cartridge 300. The first cartridge 300 may be used to generate plasma in a region with short hair, such as the skin of a short-haired pet or belly of a pet.

Figure 4A:
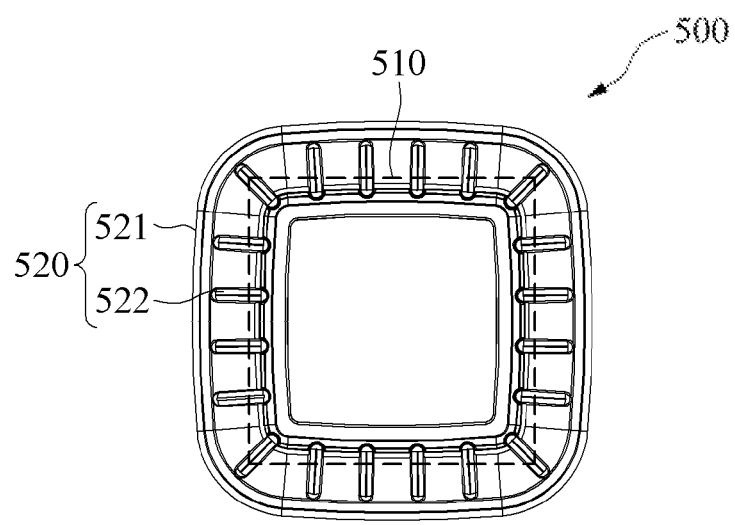
FIGS. 4A and 4B illustrates an example of a second cartridge according to some example embodiments of the present disclosure.
Figure 4B:
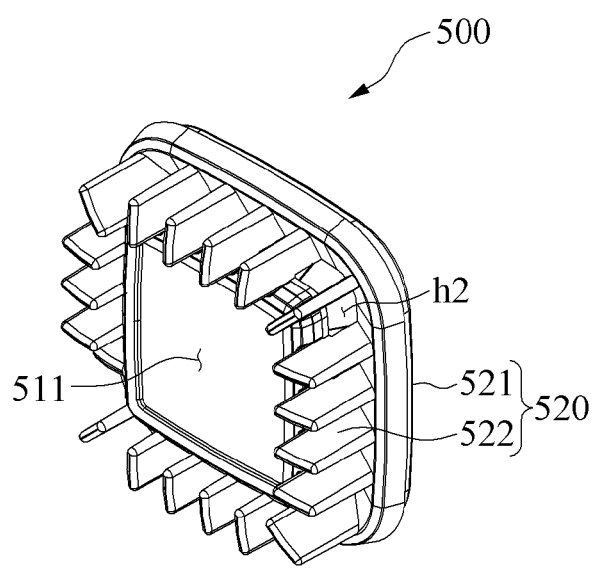

The plasma generator 1000 may include a second cartridge (e.g., second cartridge 500 of FIGS. 4A and 4B). The second cartridge may be used to generate plasma in a region with long hair, such as the skin of a long-haired pet or back of a pet.

The plasma generator 1000 may include a third cartridge (e.g., third cartridge 600 of FIGS. 5A and 5B) for irradiating plasma to the skin with curves, such as a toe. The first interface unit 110 may be provided below the first cartridge 300 to the third cartridge to receive the input from the user for controlling the first cartridge 300 to the third cartridge.

The second interface unit 120 may be provided below the light irradiation portion 400 to receive the input from the user for controlling the light irradiation portion 400.

Herein, the first interface unit 110 and the second interface unit 120 may be implemented to operate in an opposite manner to the aforementioned description. For example, the first interface unit 110 may be provided below the at least one cartridge to receive the input from the user for controlling the light irradiation portion 400. The second interface unit 120 may be provided below the light irradiation portion 400 to receive the input from the user for controlling the at least one cartridge.

The light output portion 130 may include a light emitting diode (LED). The light output portion 130 may inform the user of occurrence of an event through blinking of the LED. For example, the light output portion 130 may inform the user of an operation of at least one cartridge through blinking of the LED. As another example, the light output portion 130 may inform the user of an operation of the light irradiation portion 400 through blinking of the LED. Additionally, the light output portion 130 may vary and output a form of limit emission, an intensity of light emission, or a blinking cycle according to intensity of plasma that is generated through the plasma generator 1000.

The sound output portion 140 may output audio data, such as guidance on operation of the at least one cartridge, guidance on operation of the light irradiation portion 400, or sound effect. The sound output portion 140 may include a speaker or a buzzer.

The head portion 200 may include a plasma generating portion for generating plasma. The plasma may be an ionized gas and may be a fourth state of a material that follows solid, liquid, and gas. In general, plasma may be generated based on discharge of high voltage and may be used for the purpose of treatment and shaping of an epidermal portion of the skin due to a sublimation action when induced to the skin of a pet. Here, the sublimation action may refer to a phase transition phenomenon in which a substance changes from a solid to a gas without going through a liquid process in chemistry.

The plasma generated from the plasma generating portion may be irradiated to the skin of the pet through the at least one cartridge. In the present disclosure, the plasma generator 1000 may generate the plasma using a dielectric barrier discharge (DBD) method. The DBD method may be a widely used method since it is possible to generate high-powered discharge and a complex pulse power supply is built in. In detail, the DBD method may include a single metal electrode. At least one of electrodes may be covered with a dielectric layer. If an insulator is used, it is impossible to flow current through an electrode in the case of direct current (DC) power. Therefore, plasma may be generated using alternating current (AC) power. The dielectric layer may block reversing current and avoid transition to an arc, allowing an operation in a continuous pulse mode. Also, the dielectric layer may induce uniform discharge of plasma by randomly distributing electrons accumulated on the surface.

The first cartridge 300 may detachably couple at a first end of the head portion 200 and may generate plasma over a predetermined region. Herein, the first cartridge 300 may be a cartridge for irradiating plasma to a region with short hair, such as skin of a short-haired pet or belly of a pet.

In detail, the first cartridge 300 may include a first edge frame configured to form at least a portion of an outer appearance of the first cartridge 300 and detachably formed at the first end of the head portion 200 and a plurality of first protruding portions formed in the first edge frame. The plurality of first protruding portions may be formed in the first edge frame at preset intervals. The user may comb the hair of the pet through the plurality of first protruding portions formed at preset intervals. The user may treat skin inflammation or exterminate bacteria and mites by irradiating the plasma to the skin of the pet. An example of the first cartridge 300 according to the present disclosure is described below with reference to FIGS. 3A and 3B.

Herein, the plasma generator 1000 may include the second cartridge used to generate plasma in a region with long hair, such as the skin of a long-haired pet or back of a pet. The second cartridge may detachably couple at the first end of the head portion 200 and may generate plasma over the predetermined region. The user may expose the skin of the pet by combing the hair of the pet through the plurality of second protruding portions provided to the second cartridge. The user may irradiate plasma to the exposed skin of the pet. If necessary, the user may use the first cartridge 300 by coupling the first cartridge 300 to the head portion 200 or may use the second cartridge by coupling the second cartridge to the head portion 200. An example of the second cartridge according to the present disclosure is described below with reference to FIGS. 4A and 4B.

Herein, the plasma generator 1000 may include the third cartridge for irradiating plasma to the skin with curves, such as a toe. The third cartridge may detachably couple at the first end of the head portion 200 and may generate plasma over the predetermined region. If necessary, the user may use the third cartridge by coupling the third cartridge to the head portion 200. An example of the third cartridge according to the present disclosure is described below with reference to FIGS. 5A and 5B.

The light irradiation portion 400 may be provided at a second end of the head portion 200. Here, the second end may be the other end of the head portion 200 to which the at least one cartridge couples.

The light irradiation portion 400 may irradiate light to the inside of the ear of the pet. The user may exterminate bacteria or germs that may be present inside the ear of the pet by irradiating the light to the inside of the ear of the pet through the light irradiation portion 400. Alternatively, the user may soothe the skin by irradiating the light to the inside of the ear of the pet through the light irradiation portion 400. Alternatively, the light irradiation portion 400 may irradiate the light to the skin, such as back and belly of the pet, or sole of the pet's foot. An example of the light irradiation portion 400 according to the present disclosure is described below with reference to FIGS. 6A and 6B.

The plasma generator 1000 may be charged with a charging portion 2000. The user may charge power for driving the plasma generator 1000 by coupling the plasma generator 1000 to the charging portion 2000. Alternatively, the plasma generator 1000 may have a separate charging port for charging power.

According to the aforementioned configuration, the plasma generator 1000 may irradiate plasma to the skin of the pet through the at least one cartridge. The at least one cartridge may include the first cartridge 300, the second cartridge, and the third cartridge used for different purposes. The user may irradiate plasma by selecting an appropriate cartridge from among the first cartridge 300 to the third cartridge according to species of the pet, a hair state of the pet, or a region to which plasma is to be irradiated. Conventionally, a plurality of plasma generators having different functions need to be provided to perform an appropriate procedure according to a region. However, in the plasma generator 1000 according to the present disclosure, the first cartridge 300 to the third cartridge may detachably couple to the head portion 200. That is, since the user does not need to purchase a plurality of plasma generators, cost for purchasing a plasma generator may be saved. Also, the plasma generator 1000 according to the present disclosure may also have the light irradiation portion 400 in addition to the at least one cartridge for generating plasma. Therefore, cost used for the user to purchase devices for managing the skin of the pet may be further saved.

Hereinafter, at least one cartridge and the light irradiation portion 400 according to the present disclosure are described with reference to FIGS. 3 to 7.

Figure 3A:
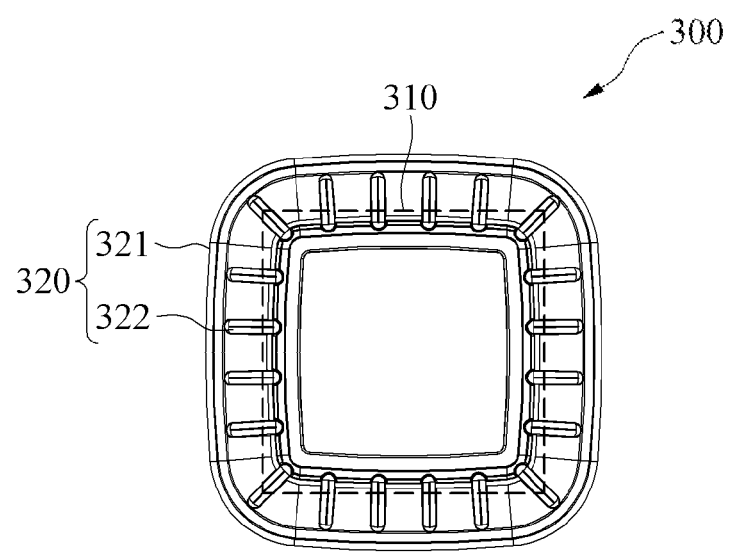
FIGS. 3A and 3B illustrates an example of a first cartridge according to some example embodiments of the present disclosure.
Figure 3B:
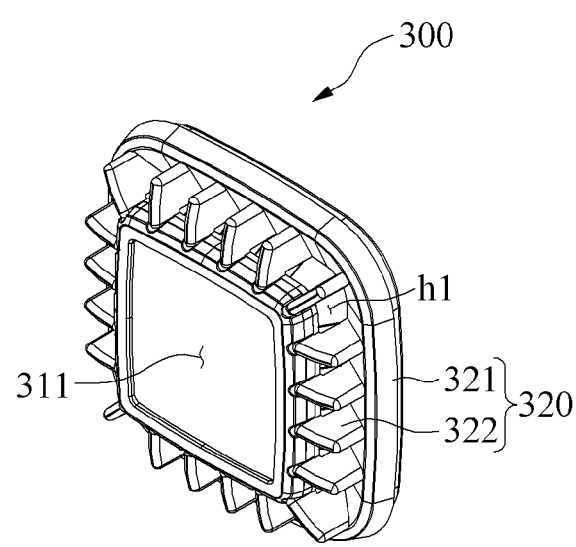

FIGS. 3A and 3B illustrates an example of a first cartridge according to some example embodiments of the present disclosure. FIG. 3A is a front view illustrating an example of a first cartridge according to some example embodiments of the present disclosure. FIG. 3B is a perspective view illustrating an example of a first cartridge according to some example embodiments of the present disclosure. The first cartridge 300 may be a cartridge for irradiating plasma to a region with short hair, such as the skin of a short-haired pet or belly of a pet.

Referring to FIGS. 3A and 3B, the first cartridge 300 may include a first operating portion 310 and a first coupling portion 320.

The first operating portion 310 may irradiate plasma to a region that faces a first operation surface 311 through the first operation surface 311.

For example, the plasma generator 1000 according to the present disclosure may employ a DBD method. The plasma generator 1000 may irradiate plasma generated through the DBD method to the skin of a pet through the first operation surface 311. The first operation surface 311 may be formed as a flat or approximately flat surface. The plasma generator 1000 may induce substantially uniform irradiation of plasma through the first operation surface 311.

The first coupling portion 320 may couple to the first operating portion 310 and may detachably couple to the head portion 200. The first coupling portion 320 may include a first edge frame 321 and a plurality of first protruding portions 322.

The first edge frame 321 may be formed to be detachable to edge of the first end of the head portion 200.

The plurality of first protruding portions 322 may be formed in the first edge frame 321 and may couple to a side surface of the first operating portion 310. Here, the plurality of first protruding portions 322 may be formed in the first edge frame 321 to not protrude forward of the first operating portion 310. For example, the first cartridge 300 may be a cartridge for irradiating plasma to the skin of a short-haired pet. The plurality of first protruding portions 322 may be formed to not protrude forward of the first operating portion 310 such that the user may comb the hair of the short-haired pet.

Herein, as the plurality of first protruding portions 322 couple to the side surface of the first operating portion 310 at preset intervals, first suction holes (h1) may be formed in the first cartridge 300. Through the first suction holes (h1) formed in the first cartridge 300, the plasma generator 1000 may suck ozone ($O_3$) that is generated as plasma is irradiated to the skin.

In detail, when plasma is irradiated to the skin of the pet, it may have adverse effect on a human and, further, ozone with odor may be generated. To remove such ozone. The plasma generator 1000 may include an ozone removal portion. For example, the ozone removal portion may include a suction fan for sucking ozone. As the suction fan operates, ozone may be sucked into the inside of the plasma generator 1000 through the first suction holes (h1) formed in the first cartridge 300. Therefore, an owner of the pet may safely irradiate plasma to the skin of the pet. Also, plasma may be irradiated to the outside through the first operation surface 311 and accordingly, ozone may be generated in the vicinity of the first operation surface 311. Therefore, when the first suction holes (h1) are formed by the plurality of first protruding portions 322 that couple to the side surface of the first operating portion 310 at preset intervals, the generated ozone may be efficiently sucked through the first suction holes (h1). An example of the ozone removal portion according to the present disclosure is described below with reference to FIGS. 7 and 8.

According to the aforementioned configuration, the plasma generator 1000 may include the first cartridge 300 that detachably couples to the head portion 200. The first cartridge 300 may include the plurality of first protruding portions 322 that couple to the side surface of the first operating portion 310 at preset intervals. As the plurality of first protruding portions 322 are provided at preset intervals, the user may comb the hair of the pet through the plurality of first protruding portions 322. Also, since the first protruding portion 322 does not protrude further forward of the first operating portion 310, a distance between the operation surface 311 and the skin may be prevented from being excessively far in a region in which the hair of the pet is short.

In the case of irradiating plasma to the hair of the pet without combing the hair of the pet, although plasma is irradiated to the pet, the irradiated plasma may not reach the skin of the pet. In this case, although plasma is irradiated, effect of treatment may be insignificant. Therefore, the first cartridge 300 according to the present disclosure may include the plurality of first protruding portions 322 that couple to the side surface of the first operating portion 310 at preset intervals. Therefore, the user may expose the skin of the pet by combing the hair of the pet and may irradiate plasma to the exposed skin.

Meanwhile, according to some example embodiments of the present disclosure, the plasma generator 1000 may include the second cartridge for irradiating plasma to the skin of a long-haired pet. An example of the second cartridge according to the present disclosure is described below with reference to FIGS. 4A and 4B.

FIGS. 4A and 4B illustrates an example of a second cartridge according to some example embodiments of the present disclosure. FIG. 4A is a front view illustrating an example of a second cartridge according to some example embodiments of the present disclosure. FIG. 4B is a perspective view illustrating an example of a second cartridge according to some example embodiments of the present disclosure. The second cartridge 500 may be a cartridge for irradiating plasma to the skin of a long-haired pet.

Referring to FIGS. 4A and 4B, a second cartridge 500 may include a second operating portion 510 and a second coupling portion 520.

The second operating portion 510 may irradiate plasma to a region that faces a second operation surface 511 through the second operation surface 511.

For example, the plasma generator 1000 according to the present disclosure may employ a DBD method. The plasma generator 1000 may irradiate plasma generated through the DBD method to the skin of a pet through the second operation surface 511. The second operation surface 511 may be formed as a flat or approximately flat surface. The plasma generator 1000 may induce substantially uniform irradiation of plasma through the second operation surface 511.

The second coupling portion 520 may couple to the second operating portion 510 and may detachably couple to the head portion 200. The second coupling portion 520 may include a second edge frame 521 and a plurality of second protruding portions 522.

The second edge frame 521 may be formed to be detachable to edge of the first end of the head portion 200.

The plurality of second protruding portions 522 may be formed in the second edge frame 521 and may couple to a side surface of the second operating portion 510. Here, the plurality of second protruding portions 522 may be formed in the second edge frame 521 to protrude forward of the second operating portion 510. For example, the second cartridge 500 may be a cartridge for irradiating plasma to the skin of a long-haired pet. The plurality of second protruding portions 522 may be formed to protrude forward of the second operating portion 510 such that the user may comb the hair of the long-haired pet. The second protruding portion 522 may protrude forward of the second operating portion 510 and accordingly, the skin may be effectively exposed for the second operation surface 511 in a region with long hair of the pet.

Herein, as the plurality of second protruding portions 522 is coupled to the side surface of the second operating portion 510 at preset intervals, second suction holes (h2) may be formed in the second cartridge 500. The plasma generator 1000 may suck ozone that is generated as plasma is irradiated to the skin through the second suction holes (h2) formed in the second cartridge 500.

According to the aforementioned configuration, the plasma generator 1000 may include the second cartridge 500 configured to detachably couple to the head portion 200. The second cartridge 500 may include the plurality of second protruding portions 522 configured to couple to the side surface of the second operating portion 510 at preset intervals. As the plurality of second protruding portions 522 are provided at preset intervals, the user may comb the hair of the pet through the plurality of second protruding portions 522. The user may expose the skin of the pet by combing the hair of the pet and may irradiate plasma to the exposed skin. Also, the plurality of second protruding portions 522 may protrude forward of the second operating portion 510. That is, a length at which the plurality of second protruding portions 522 protrude from the second edge frame 521 may be longer than that of the plurality of first protruding portions 322 of the first cartridge 300. Therefore, the plurality of second protruding portions 522 may be suitable for coming the hair of the long-haired pet. According to a hair state of the pet, the user may use the first cartridge 300 having the plurality of first protruding portions 322 or may use the second cartridge 500 having the plurality of second protruding portions 522.

Meanwhile, according to some example embodiments of the present disclosure, the plasma generator 1000 may include the third cartridge for irradiating plasma to the skin with curves, such as a toe. An example of the third cartridge according to the present disclosure is described with reference to FIGS. 5A and 5B.

Figure 5A:
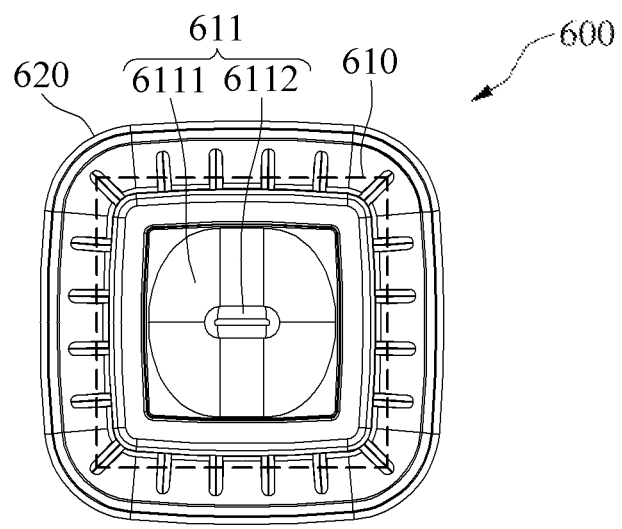
FIGS. 5A and 5B illustrates an example of a third cartridge according to some example embodiments of the present disclosure.
Figure 5B:
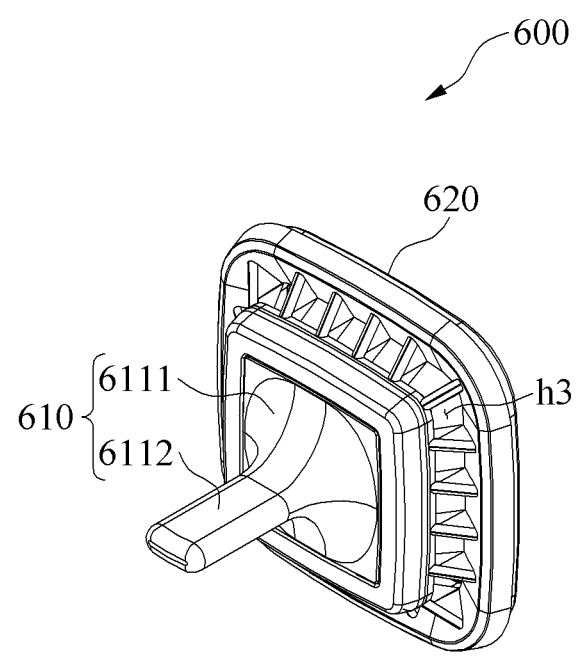

FIGS. 5A and 5B illustrates an example of a third cartridge according to some example embodiments of the present disclosure. FIG. 5A is a front view illustrating an example of a third cartridge according to some example embodiments. FIG. 5B is a perspective view illustrating an example of a third cartridge according to some example embodiments. A third cartridge 600 may be a cartridge for irradiating plasma to the skin with curves, such as a toe.

Referring to FIGS. 5A and 5B, the third cartridge 600 may include a third operating portion 610 and a third coupling portion 620.

The third operating portion 610 may irradiate plasma to a region that faces a third operation surface 611 through the third operation surface 611.

For example, the plasma generator 1000 according to the present disclosure may employ a DBD method. The plasma generator 1000 may irradiate plasma that is generated using the DBD method to the skin of a pet through the third operation surface 611.

The third operation surface 611 may include a (3-1)-th operation surface 6111 and a (3-2)-th operation surface 6112. The (3-1)-th operation surface 6111 may refer to a surface that forms at least a portion of the third operation surface 611. The (3-1)-th operation surface 6111 may be an approximately flat surface except for a protruding pillar that protrudes from the (3-1)-th operation surface 6111. The (3-2)-th operation surface 6112 may be a surface that corresponds to a surface of the protruding pillar that protrudes from the (3-1)-th operation surface 6111. The (3-1)-th operation surface 6111 and the (3-2)-th operation surface 6112 may be surfaces on which plasma is generated in all regions. Plasma that is generated through the plasma generating portion of the head portion 200 may be irradiated to the skin of the pet through the (3-1)-th operation surface 6111 and the (3-2)-th operation surface 6112.

The third coupling portion 620 may couple to the third operating portion 610 and may detachably couple to the head portion 200.

Herein, the third coupling portion 620 may include third suction holes (h3). The plasma generator 1000 may suck ozone that is generated as plasma is irradiated to the skin of the pet through the third suction holes (h3) formed in the third coupling portion 620.

According to the aforementioned configuration, the plasma generator 1000 may include the third cartridge 600 configured to detachably couple to the head portion 200. The third cartridge 600 may include the third operation surface 611 on which plasma is generated. Depending on example embodiments, the third operation surface 611 may include the (3-1)-th operation surface 6111 and the (3-2)-th operation surface 6112. Here, the (3-2)-th operation surface 6112 may be a surface corresponding to a surface of the protruding pillar that protrudes from the (3-1)-th operation surface 6111. Feet of pets may look similar to hands or feet of humans. Feet of pets may include soles and toes and the skin may be present between the toes. That is, like humans, the side of toes of pets may also be the skin. It may be difficult to irradiate plasma between the toes through the first operation surface 311 of the first cartridge 300 or the second operation surface 511 of the second cartridge 500 since a gap between the toes may be somewhat small. On the contrary, the third cartridge 600 may include the protruding pillar that protrudes from the (3-1)-th operation surface 6111. Plasma may be generated on the (3-2)-th operation surface 6112 corresponding to the surface of the protruding pillar. Therefore, the user may easily irradiate plasma even to the skin present between toes of the pet through the (3-2)-th operation surface 6112.

Meanwhile, according to some example embodiments of the present disclosure, the plasma generator 1000 may include the light irradiation portion 400 for reducing bacteria or fungi present in the ear of the pet. The user may prevent generation of bacteria or fungi or may reduce the already generated bacteria or fungi by irradiating light to the inside of the ear of the pet through the light irradiation portion 400. Hereinafter, an example of the light irradiation portion 400 according to the present disclosure is described with reference to FIGS. 6A and 6B.

Figure 6A:
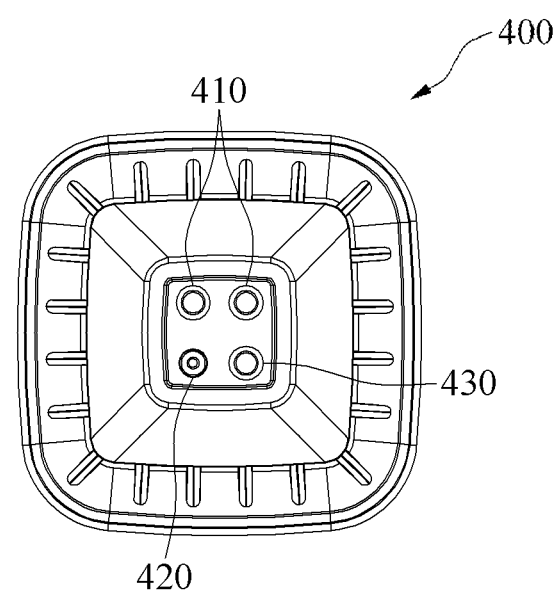
FIGS. 6A and 6B illustrates an example of a light irradiation portion according to some example embodiments of the present disclosure.
Figure 6B:
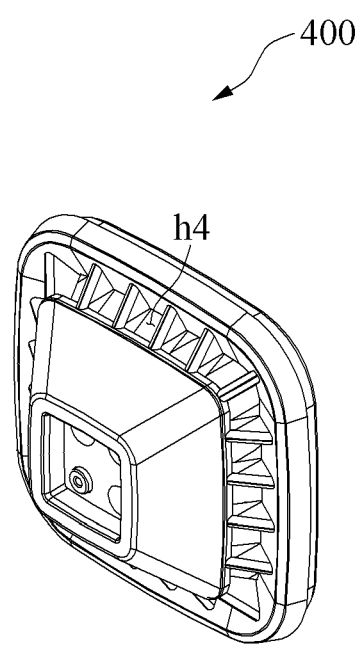

FIGS. 6A and 6B illustrates an example of a light irradiation portion according to some example embodiments of the present disclosure. FIG. 6A is a front view illustrating an example of a light irradiation portion according to some example embodiments. FIG. 6B is a perspective view illustrating an example of a light irradiation portion according to some example embodiments of the present disclosure.

Referring to FIGS. 6A and 6B, the light irradiation portion 400 may include at least one first light emitting diode (LED) 410, at least one first laser diode (LD) 420, and at least one second LED 430.

Each of the at least one first LED 410, the at least one first LD 420, and the at least one second LED 430 may generate light using a different wavelength.

For example, the at least one first LED 410 may sterilize the ear of a pet by generating light having a first wavelength of 355 nm to 455 nm. The at least one first LD 420 may treat the skin of the pet's ear or may suppress inflammation by generating light having a second wavelength of 640 nm to 655 nm. The at least one second LED 430 may suppress inflammation of the pet's ear and may reduce bacteria by generating light having a third wavelength of 660 nm to 670 nm. Therefore, the user may irradiate complex light to the ear of the pet through the light irradiation portion 400 and may manage a variety of diseases at a time. Depending on example embodiments, the user may selectively operate each of the at least one first LED 410, the at least one first LD 420, and the at least one second LED 430 through the second interface unit 120.

According to some example embodiments of the present disclosure, the light irradiation portion 400 may include a plurality of third protruding portions configured to protrude from a third edge frame that couples to the head portion 200. The user may insert the plurality of third protruding portions into the ear of the pet and then may irradiate light to the inside of the pet's ear through the light irradiation portion 400.

Herein, the light irradiation portion 400 may also irradiate light to the skin, such as back, belly, or sole of the pet. The user may treat the skin of the pet or may reduce pain caused by inflammation by irradiating light to the skin of the pet through the light irradiation portion 400.

Herein, the light irradiation portion 400 may include discharge holes (h4). The plasma generator 1000 may discharge ozone that is generated as plasma is irradiated to the skin, through the discharge holes (h4) formed in the light irradiation portion 400.

In detail, the light irradiation portion 400 may be provided at a second end of the head portion 200. The second end may be the other end of the head portion 200 to which the at least one cartridge is provided. The head portion 200 provided between the at least one cartridge and the light irradiation portion 400 may include a suction fan for sucking ozone. When plasma is generated from the at least one cartridge, the suction fan may operate. As the suction fan operates, ozone that is generated as plasma is irradiated to the skin of the pet may be sucked into the inside of the head portion 200 through suction holes provided to the at least one cartridge. Ozone sucked into the inside of the head portion 200 may be discharged to the outside through the discharge holes (h4) provided to the light irradiation portion 400. According to some example embodiments of the present disclosure, the plasma generator 1000 may remove ozone sucked into the inside of the head portion 200. The plasma generator 1000 may discharge gas that is unharmful to humans since ozone is removed to the outside through the discharge holes (h4). Hereinafter, an example of the ozone removal portion according to the present disclosure is described with reference to FIGS. 7 and 8.

Figure 7:
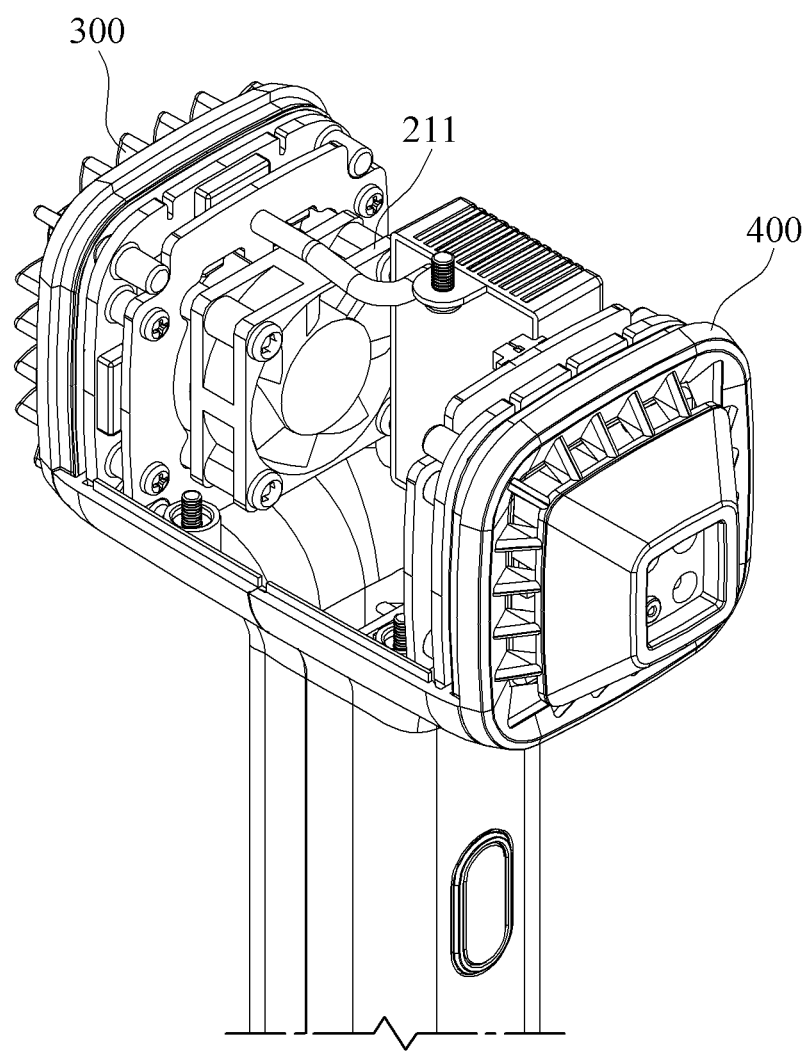
FIG. 7 illustrates a positional relationship of an ozone removal portion according to some example embodiments of the present disclosure.
Figure 8:
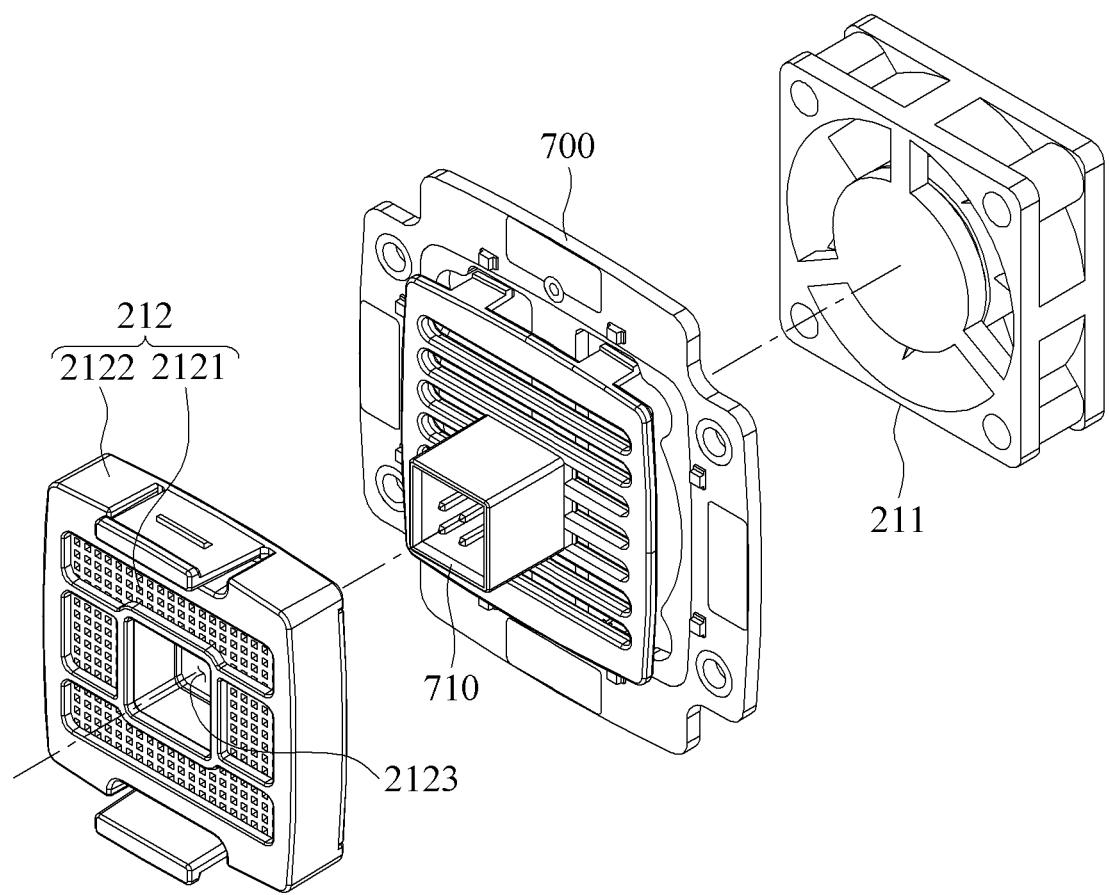
FIG. 8 illustrates an example of an ozone removal portion according to some example embodiments of the present disclosure.

FIG. 7 illustrates a positional relationship of an ozone removal portion according to some example embodiments of the present disclosure. FIG. 8 illustrates an example of an ozone removal portion according to some example embodiments of the present disclosure.

According to some example embodiments of the present disclosure, the plasma generator 1000 may include the ozone removal portion. The ozone removal portion may be located at the rear of the first cartridge 300. The ozone removal portion may suck ozone that is generated as plasma is irradiated to the skin through the first cartridge 300. The ozone removal portion may include the suction fan 211 for sucking ozone. When the suction fan 211 operates, ozone may be sucked into the inside of the plasma generator 1000 through the first suction holes (h1) formed in the first cartridge 300. Therefore, an owner of a pet may safely irradiate plasma to the skin of the pet.

According to some example embodiments of the present disclosure, the suction fan 211 may suck ozone based on an input from the user. For example, the suction fan 211 may operate in conjunction with the input from the user through the first interface unit 110 for operating at least one cartridge. That is, when the at least one cartridge operates, the suction fan 211 may also operate. When the suction fan 211 operates, ozone may be sucked into the inside of the head portion 200 through suction holes formed in the at least one cartridge.

Referring to FIG. 8, the ozone removal portion may further include an ozone filtering portion 212 for removing ozone sucked by the suction fan 211.

The ozone filtering portion 212 may include an ozone filter 2121 configured to remove ozone and a first filter case 2122 configured to fix the ozone filter 2121. The ozone filter 2121 may be a mesh-typed filter. Alternatively, the ozone filter 2121 may be a block-typed filter using catalyst. The first filter case 2122 may detachably couple to the gripping portion 100. The user may replace the first filter case 2122 and the ozone filter 2121 by decoupling the first filter case 2122. Alternatively, the ozone filter 2121 may detachably insert into the first filter case 2122. The user may separate, from the first filter case 2122, and replace the ozone filter 2121.

According to some example embodiments of the present disclosure, the ozone filtering portion 212 may include a plurality of carbon beads configured to remove ozone and a second filter case configured to fix the carbon beads. The plurality of carbon beads may be grains of a porous carbon material. When ozone is sucked according to an operation of the suction fan 211, the plurality of carbon beads may suck or remove the sucked ozone.

According to some example embodiments of the present disclosure, a scent may be added to the ozone filtering portion 212 such that pets may feel comfortable. For example, an aroma-based fragrance may be added to the ozone filtering portion 212.

According to some example embodiments of the present disclosure, a plasma generating portion 700 may be provided between the ozone filtering portion 212 and the suction fan 211. The plasma generating portion 700 may be connected to the first operating portion 310. Plasma generated through the plasma generating portion 700 may be irradiated to the skin of the pet through the first operating portion 310.

The plasma generating portion 700 may include a connecting portion 710 configured to protrude from one surface that faces the first operating portion 310 for connection to the first operating portion 310. The connecting portion 710 of the plasma generating portion 700 may be connected to the first operating portion 310 by passing through the ozone filtering portion 212. For example, the ozone filtering portion 212 may be provided between the plasma generating portion 700 and the first operating portion 310. The ozone filtering portion 212 may include a hollow through which the connecting portion 710 passes. The connecting portion 710 of the plasma generating portion 700 may pass through the hollow provided to the ozone filtering portion 212 and may be connected to the first operating portion 310.

As described above with reference to FIGS. 1 to 8, the plasma generator 1000 may irradiate plasma to the skin of the pet through at least one cartridge. The at least one cartridge may include the first cartridge 300, the second cartridge 500, and the third cartridge 600 used for different purposes. The user may select an appropriate cartridge from among the first cartridge 300, the second cartridge 500, and the third cartridge 600 according to a hair state of the pet or a region to which plasma is to be irradiated, and may irradiate the plasma.

Also, the plasma generator 1000 may irradiate light to the ear of the pet through the light irradiation portion 400. The light irradiation portion 400 may include a plurality of LEDs having different wavelengths and accordingly, the user may simultaneously manage various diseases.

Description related to the proposed example embodiments is provided such that one skilled in the art may use or implement the present disclosure. It will be apparent to one skilled in the art that various modifications may be made to the example embodiments without departing from the scope of the present disclosure. Herein, the general principles may be applied to other example embodiments without departing from the scope of the present disclosure. Therefore, the present disclosure is not limited to the example embodiments and should be interpreted within the widest scope consistent with the principles and novel features presented herein.

What is claimed is:

1. A plasma generator comprising:
   a gripping portion comprising at least one interface unit configured to receive an input from a user;
   a head portion comprising a plasma generating portion configured to generate the plasma;
   a first cartridge configured to detachably couple at a first end of the head portion and generate the plasma over a predetermined region; and
   a light irradiation portion provided at a second end of the head portion,
   wherein at least one suction hole for sucking ozone ($O_3$) that is generated as the plasma is irradiated to a skin is formed in the first cartridge,
   the head portion comprises an ozone removal portion for removing the ozone,
   the ozone removal portion comprises a suction fan for sucking the ozone and an ozone filtering portion for removing the sucked ozone, and
   the light irradiation portion comprises a plurality of discharge holes for discharging gas in which the ozone is removed by passing through the ozone filtering portion.

2. The plasma generator of claim 1, wherein the at least one interface unit comprises:
   a first interface unit configured to receive an input from the user for controlling the first cartridge; and
   a second interface unit configured to receive an input from the user for controlling the light irradiation portion.

3. The plasma generator of claim 1, wherein the first cartridge comprises:
a first operating portion configured to irradiate the plasma to a region that faces a first operation surface through the first operation surface; and
a first coupling portion configured to couple to the first operating portion and detachably couple to the head portion, and
the first coupling portion comprises:
a first edge frame formed to be detachable to an edge of the first end of the head portion; and
a plurality of first protruding portions formed in the first edge frame and configured to couple to a side surface of the first operating portion, the plurality of first protruding portions being formed in the first edge frame to not protrude forward of the first operating portion.

4. The plasma generator of claim 1, further comprising:
a second cartridge configured to detachably couple at the first end of the head portion and generate the plasma over the predetermined region,
wherein the second cartridge comprises:
a second operating portion configured to irradiate the plasma to a region that faces a second operation surface through the second operation surface; and
a second coupling portion configured to couple to the second operating portion and detachably couple to the head portion, and
the second coupling portion comprises:
a second edge frame formed to be detachable to an edge of the first end of the head portion; and
a plurality of second protruding portions formed in the second edge frame and configured to couple to a side surface of the second operating portion, the plurality of second protruding portions formed in the second edge frame to protrude forward of the second operating portion.

5. The plasma generator of claim 1, further comprising:
a third cartridge configured to detachably couple at the first end of the head portion and generate the plasma over the predetermined region,
wherein the third cartridge comprises:
a third operating portion configured to irradiate the plasma to a region that faces a third operation surface through the third operation surface; and
a third coupling portion configured to couple to the third operating portion and detachably couple to the head portion, and
the third operation surface comprises:
a first operation sub-surface; and
a second operation sub-surface corresponding to a surface of a protruding pillar that protrudes from the first operation sub-surface.

6. The plasma generator of claim 1, wherein the light irradiation portion comprises:
at least one first light emitting diode (LED) using a first wavelength;
at least one first laser diode (LD) using a second wavelength different from the first wavelength; and
at least one second LED using a third wavelength different from the first wavelength and the second wavelength.

7. The plasma generator of claim 1, wherein the ozone filtering portion comprises:
an ozone filter configured to remove the ozone; and
a first filter case configured to fix the ozone filter.

8. The plasma generator of claim 1, wherein the ozone filtering portion comprises:
a plurality of carbon beads configured to remove the ozone; and
a second filter case configured to fix the carbon beads.

9. The plasma generator of claim 3, wherein the plasma generating portion comprises a connecting portion configured to protrude from one surface that faces the first operating portion for connection to the first operating portion, and
the ozone filtering portion is provided between the plasma generating portion and the first operating portion and comprises a hollow portion through which the connecting portion passes.

10. The plasma generator of claim 3, wherein the plurality of first protruding portions are configured to couple to a side surface of the first operating portion at preset intervals such that the ozone is sucked according to an operation of the suction fan.

* * * * *